United States Patent
Snook

[11] Patent Number: 5,545,129
[45] Date of Patent: Aug. 13, 1996

[54] SUPPORTIVE FOOT CUSHION DEVICE

[76] Inventor: Kim C. Snook, 3067 Badger Pl., Saginaw, Mich. 48603

[21] Appl. No.: 387,473

[22] Filed: Feb. 13, 1995

[51] Int. Cl.$^6$ .................................................. A61F 5/00
[52] U.S. Cl. ........................... 602/66; 128/894; 36/145; 36/161; 36/166
[58] Field of Search .................... 36/28, 91, 145, 36/161, 166; 602/66; 128/894

[56] References Cited

U.S. PATENT DOCUMENTS

| | | |
|---|---|---|
| 958,199 | 5/1910 | Ward . |
| 1,492,514 | 4/1924 | Jensen ........................................ 602/66 |
| 2,569,721 | 10/1951 | Juers .......................................... 36/145 |
| 2,619,961 | 12/1952 | Stewart . |
| 3,036,571 | 5/1962 | Scholl . |
| 3,063,448 | 11/1962 | Scholl . |
| 3,086,523 | 4/1963 | Lowth . |
| 3,088,461 | 5/1963 | Levitt . |
| 3,209,750 | 10/1965 | Levitt . |
| 3,253,591 | 5/1966 | Scholl . |
| 4,309,990 | 1/1982 | Brooks et al. ............................... 602/8 |
| 4,729,369 | 3/1988 | Cook . |
| 4,733,907 | 3/1988 | Fellenbaum ........................ 297/188.01 |
| 5,070,867 | 12/1991 | March ...................................... 36/91 X |
| 5,418,259 | 5/1995 | Broos et al. ............................. 521/159 |

Primary Examiner—Richard J. Apley
Assistant Examiner—Kim M. Lee
Attorney, Agent, or Firm—Learman & McCulloch

[57] ABSTRACT

A foot cushioning device especially adapted for use by diabetic persons suffering from a protruding joint disorder of the foot in the arch or instep region includes a thick foam pad having a notch extending into the pad from one side thereof. The pad may be positioned against the sole of a person's foot with the Charcot joint protrusion accommodated in the notch. An elastic band of non-chafing material may be secured at a first end to the lower surface of the pad by means of hooked anchoring fabric secured to the pad. The other end of the band may be wrapped around the top of the person's foot and overlapped onto the first end of the band at a location beneath the lower surface of the pad and secured in place to the band material by another swatch of the anchoring fabric provided on the overlapping end of the band. A person fitted with such a device may then place his or her foot within the confines of a shoe with the pad serving to isolate and protect the afflicted region from coming into contact with the shoe.

14 Claims, 3 Drawing Sheets

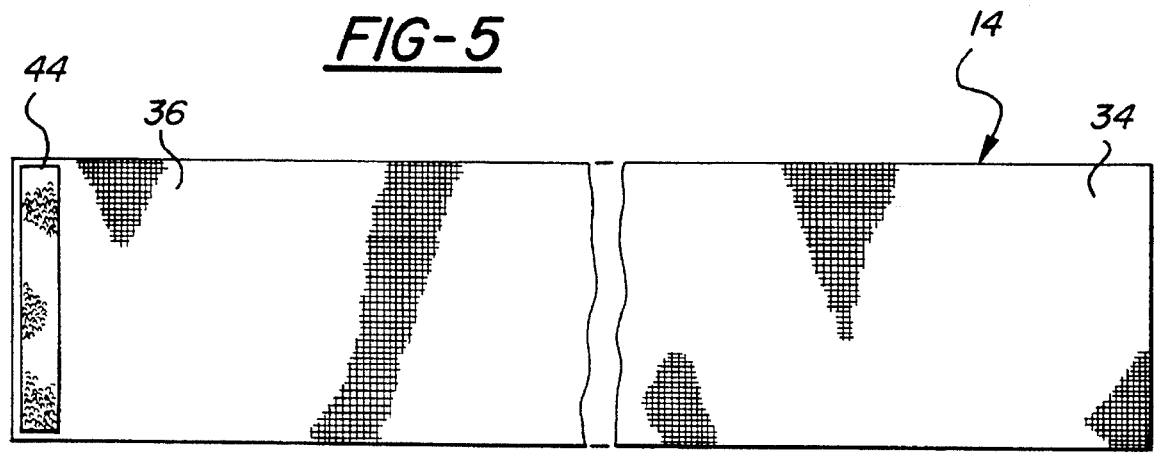
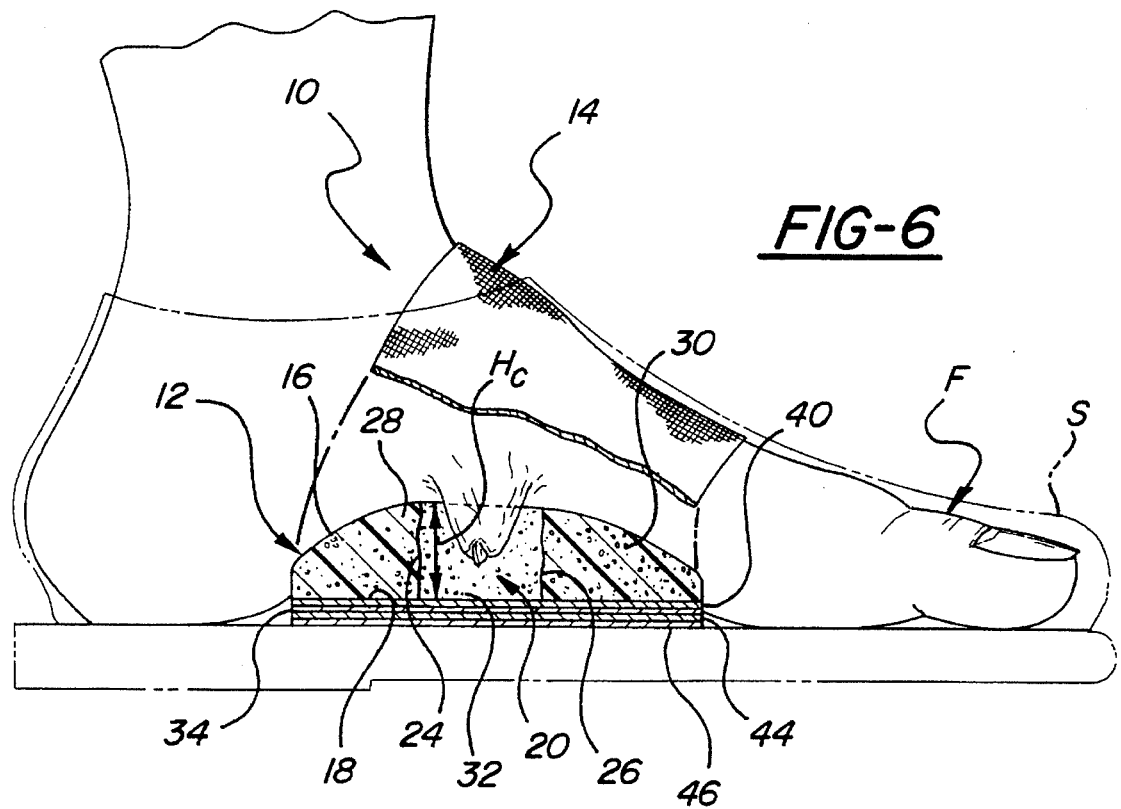

SUPPORTIVE FOOT CUSHION DEVICE

This invention relates to a foot cushion that is adapted to be applied to a person's foot for relieving pressure and discomfort associated with various afflictions of the foot.

BACKGROUND OF THE INVENTION

Cushions or pads of various sizes and kinds are known for relieving pressure and discomfort associated with various afflictions of the feet. None address the specific needs of diabetic persons suffering from a foot disorder known medically as Charcot joint. This disorder destroys the joints of the feet particularly in the arch region causing a protruding deformity to develop that, if left unprotected, is prone to ulcerate and become infected.

Diabetics often have dermatological disorders that render the skin of the person particularly sensitive and susceptible to chafing and irritation. For this reason, those pads that are secured to a user's foot by adhesive means would be unsuitable for application to the foot of the diabetic to alleviate foot afflictions. Also unsuitable would be the attachment of the pad to the foot of a diabetic using a wrap fabricated material that would chafe or irritate the skin of the patient and/or a wrap whose ends are secured at a joint in direct contact with the user's skin.

SUMMARY OF THE INVENTION

This invention overcomes the aforementioned problems and provides a cushion device that is particularly suitable for use by diabetic persons to relieve pressure and discomfort and in particularly a Charcot joint condition of the sole of a person's foot.

A device according to the invention comprises a foam pad having an elastic memory that enables the pad to deform under the weight of a person and recover its original shape after each of repeated deformations. The pad has a lateral width that approximates the width of a person's foot and an upper-foot-engaging surface that is adapted for positioning against the sole of the person's foot in the vicinity of the afflicted region. The pad has a predetermined non-compressed thickness. A notch extends inwardly from one side of the pad and between the upper and lower surfaces to provide a protective alcove for accommodation of the afflicted region. A band of non-chafing elastic material of sufficient length and elasticity may encircle both the user's foot and the pad so as to hold the pad in position against the user's foot. Attaching means are provided for securing the ends of the band at a joint underlying the lower surface of the pad so that the pad shields and protects a person's foot from direct contact with the joint.

A cushion constructed in accordance with the invention has been used successfully to alleviate the pressure and discomfort associated with a Charcot joint condition in the instep region of the foot. When the device is secured to the foot, the Charcot joint region is suspended in the notch of the pad enabling the person to wear shoes or other footwear and put weight on the foot without having the afflicted region come into direct contact with the footwear. Over time, such contact can accelerate deterioration of the joint and cause the skin of the protruding Charcot joint region to ulcerate, exposing the patient to possible infection and related complications.

With this device, a person suffering from an ulcerated Charcot joint does not have to be immobilized but can continue wearing footwear and walking. The notched pad distributes the pressure that otherwise would be applied to the afflicted region to the surrounding healthy tissue of the foot, thereby providing the proper isolated environment to promote healing of an ulcerated affliction. Just as importantly, the device prevents the recurrence of ulceration enabling the patient to maintain mobility.

Unlike previously known foot pads, this device purposely avoids the use of adhesives to secure the pad to the foot of the user. The device of this invention utilizes a non-chafing elastic band that is able to be wrapped around the upper part of the user's foot in direct contact with the skin so as to hold the pad in place without irritating or chafing the skin of the user. The ends of the band are secured in a joint that underlies the lower surface of the pad so that the pad is interposed between the joint and the user's foot thereby to isolate the user's foot from direct contact with the band joint and thus minimizing skin irritations that might otherwise be caused from direct contact with the joint.

THE DRAWINGS

The presently preferred embodiment of the invention is disclosed in the following description and in the accompanying drawings, wherein:

FIG. 5 is a fragmentary plan view of the elastic band used to secure the pad to the foot of a user; and FIG. 6 is a view partly in side elevation and partly in section of the device and showing the pad secured to the foot of a user within the confines of a shoe.

DETAILED DESCRIPTION

Figure 1:
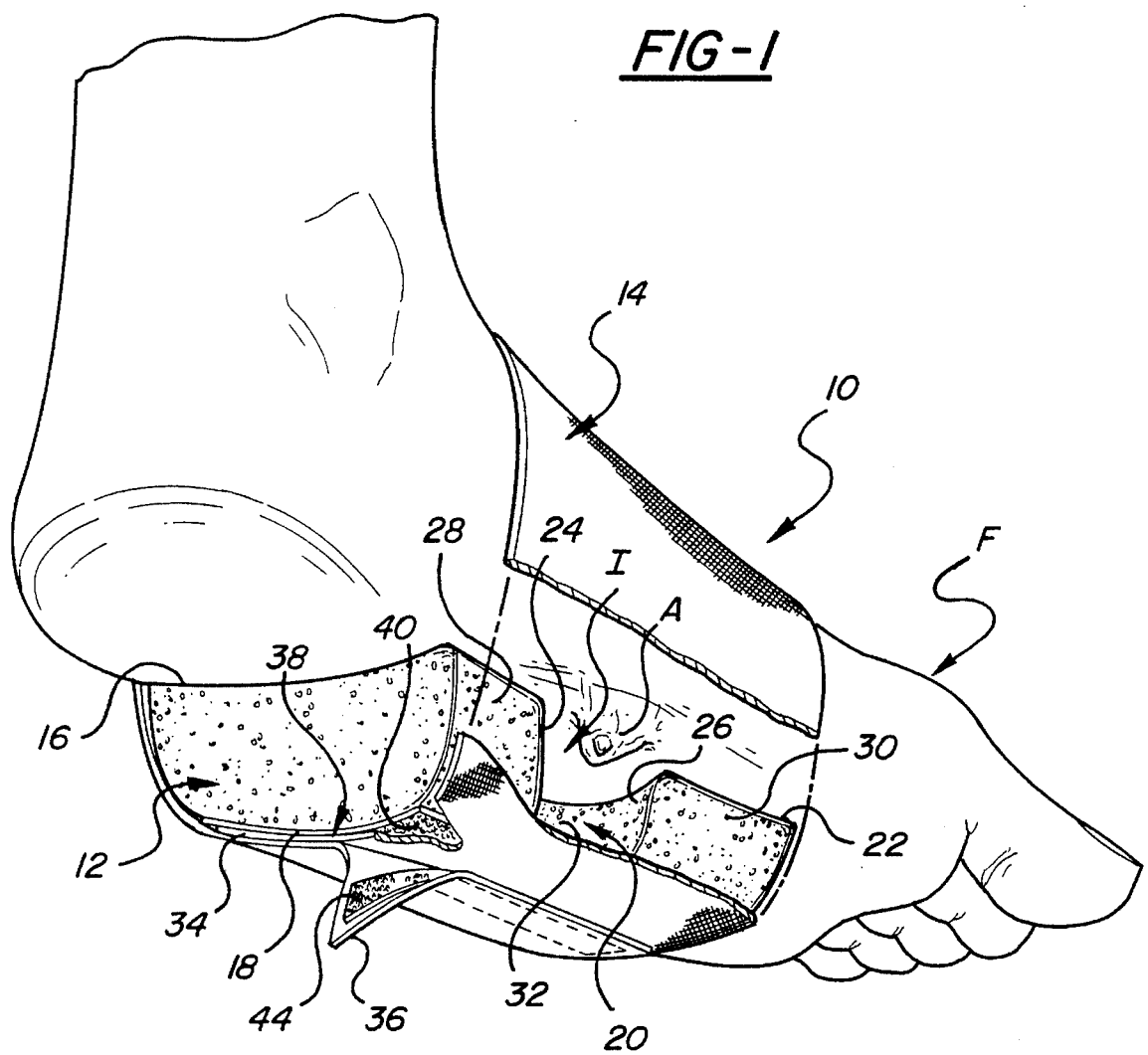
FIG. 1 is a perspective view of a device constructed according to the present invention shown partly broken away and secured to the foot of a person having a Charcot joint condition at the instep region of the foot.

A supportive foot cushion device constructed according to a presently preferred embodiment of the invention is indicated generally at 10 in the drawings and comprises a pad or block 12 of foam material that is secured to the foot of a person by an elastic band 14.

The pad 12 has an elastic memory that enables the pad to deform under the weight of a person and/or when the foot is placed in a shoe and recover its shape after each of repeated deformations. The pad is fabricated preferably of open cell polyurethane foam having a density of about 1.8 to 2.0 g/cm$^3$. The pad has a length L and width W that approximates the length and width of a user's foot in the region of the instep or arch of the foot so that when applied to the foot, the pad extends transversely across substantially the entire width of the foot and lengthwise from a point forward of the heel to a point rearward of the ball of the foot, as illustrated in FIGS. 1 and 6. A pad having a length of about 4 inches and a width of about 3 inches has been known to work well for supporting the instep region I of a person's foot F.

The preferred configuration of the pad 12 has many uses, but it is particularly suited for use by diabetic persons who suffer from a foot disorder known medically as Charcot joint. This disorder deteriorates several of the small joints in the feet typically in the instep or arch region I of a foot and, over time, calcifies and deforms the joint resulting in a characteristic bony swollen mass A that protrudes downwardly from the foot sole, as illustrated in FIGS. 1 and 6.

One of the complications of having such a Charcot joint disorder is that, if the person wears shoes or other footwear or walks with this condition, over time the resultant pressure on the afflicted joint A may damage and ulcerate the skin. Such a condition is particularly serious with diabetic patients since they are highly susceptible to infections. Consequently, patients suffering from Charcot joint disorder of the feet often are advised to stay off their feet and not wear shoes or similar footwear.

Figure 3:
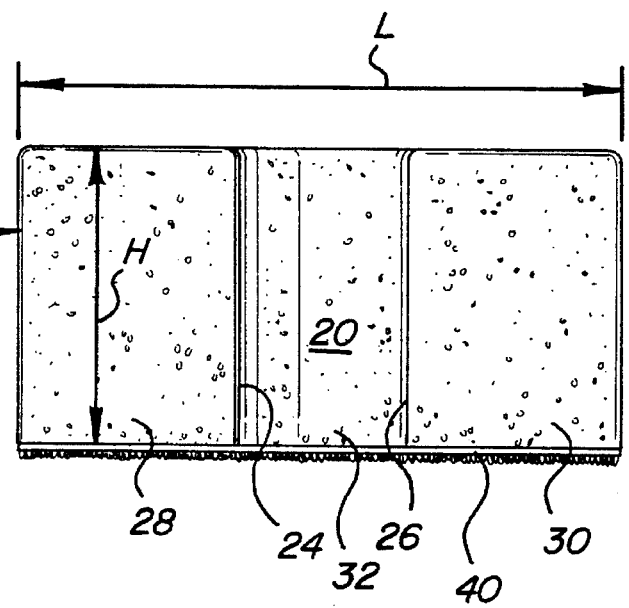
FIG. 3 is a side view of the pad of FIG. 2.
Figure 4:
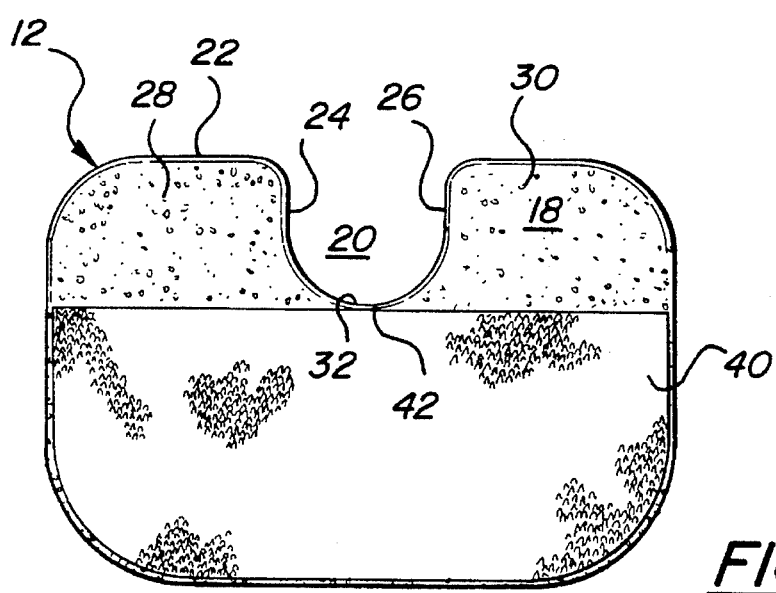
FIG. 4 is a bottom view of the pad shown in FIG. 3.

The pad 12 has been designed with this particular disorder in mind as well as other afflictions that may occur in the instep region I of a person's foot F or elsewhere. The pad 12 has an upper, relatively flat planar surface 16 adapted to be positioned against the foot 'sole in the vicinity of the affliction and has a lower, generally flat planer surface 18 that, when the foam pad is in its uncompressed free state, is generally parallel to the upper surface 16 and spaced therefrom by a distance corresponding to the uncompressed height or thickness H of the pad 12 (FIG. 3).

Figure 2:
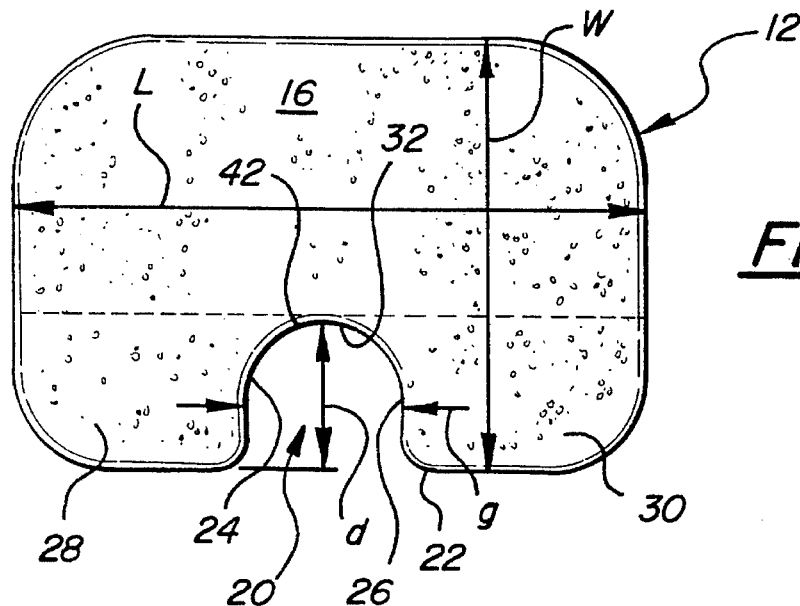
FIG. 2 is a plan view of a foam pad constructed in accordance with the present invention.

The pad 12 is formed with a notch 20 that extends laterally inwardly into the pad 12 from a side 22 thereof and between the upper and lower surfaces of the pad to provide a protective alcove or side opening in the pad 12 for the accommodation of the afflicted region A. When viewed from the upper surface (FIG. 2) the notch 20 has opposing sidewalls 24, 26 respectively, joined by an interconnecting wall 32. The distance between the walls 24, 26 preferably is about 1 inch and the walls are tangential to the interconnecting wall 32. The notch 20 extends into the pad 12 to a depth about 1 inch.

The elastic band 14 is fabricated of a washable, reusable material that will not chafe or irritate the skin of a diabetic person. The preferred material is sold commercially under the trademark "Champ" and is available from Carolon Company, Rural Hall, N.C. The band 14 has sufficient length and elasticity to encircle both the person's foot and the pad 12, as illustrated in FIGS. 1 and 6, so as to hold the pad 12 in position against the sole of the person's foot. A band 14 having a width of about 4 inches and a length of about 12 inches is preferred.

The free ends of the band 34, 36 are secured to form a joint 38 that underlies the lower surface 18 of the pad 12 so as to isolate and protect the user's foot F from coming into direct contact with the joint 38.

As shown best in FIG. 1, the joint 38 includes a first swatch or section of hooked anchoring fabric material 40 that is compatible with the band material 14, such as that sold commercially under the trademark "Velcro." The swatch 40 is glued or otherwise suitably adhered to the lower surface of the pad 12 and 18, and extends widthwise from the base 42 of the notch 20 to the opposite side of the pad 12 and spans the full length of the pad 12. The leg sections 28 and 30 adjacent the notch 20 are devoid of the hooked fabric material 40 or any other means to secure the pad 12 to the band 14 for reasons to be explained below.

The compatibility of the hooked anchoring fabric 40 and the band of material 14 enables the user to attach a first end 34 of the band 14 to the first swatch 40 in order to anchor the first end 34 releasably to the pad 12, as illustrated in FIG. 1. Once the end 34 is anchored, the other end 36 of the band 14 may be wrapped around the top of the user's foot, as illustrated in FIG. 1, and overlapped onto the first end 34 beneath the lower surface 18 at the pad 12. The end 36 mounts another swatch 42 of the same hooked fabric material so that when the end 36 is wrapped overtop the first end 34, the hooked fabric of the second swatch 42 attaches itself releasably to the band material thereby to secure the other end 36 and retain the pad 12 on the foot of the user. As illustrated in FIGS. 1 and 6, the points of attachment of the ends 34 and 36 of the band 14 underlie the lower surface 18 of the pad 12 so that the pad 12 cushions and isolates the user's foot F from coming into direct contact with the ends of the band and the means employed to secure the ends in place.

Once the pad 12 is attached to the foot F in the manner illustrated in FIG. 1, the user may, if desired, position his or her foot within a shoe S, as illustrated in FIG. 6, or other footwear. The pad 12 is selected to have a thickness or height H that is sufficient to require the pad 12 to be compressed somewhat as the foot F is fitted into the shoe S. Due to the contour of the foot, particularly in the arch region, the compression of the pad 12 is not uniform and is compressed the least in the vicinity of the affliction A, as illustrated in FIG. 6. The purpose of the pad 12 and its notch 20 is to support the arched region of the foot and particularly the afflicted region off the base of the shoe to prevent it from otherwise coming into contact with the base of the shoe S thereby to transfer the force that would otherwise be exerted on the afflicted region A to the surrounding healthy tissue of the foot that is in contact with the upper surface 16 of the pad 12. Accordingly, the density and height or thickness H of the pad 12 are so selected as to enable the pad to support and suspend the afflicted region A free of contact with a shoe or other support surface when the pad 12 is compressed under the weight of the person to its associated compressed height $H_c$, illustrated in FIG. 6. For the type and density of foam padding mentioned above, an uncompressed pad thickness of 2 inches is preferred and has been shown to work well in keeping a Charcot joint affliction A from contacting the base of a shoe S, as illustrated in FIG. 6.

As mentioned, the sections 28, 30 of the pad 12 adjacent the notch 20 are free of the hooked fabric material 40 or any other means of securing them to the band material 14. This permits the sections 28, 30 to move somewhat in relation to the band 14. Specifically, as the pad 12 is compressed between the foot F and shoe S, the resulting forces urge the sections 28 and 30 apart somewhat and widen the distance between the sidewalls 24 and 26 of the notch 20. Such movement of the sections 28, 30 and the associated widening of the notch 20 assures that the foam pad 12 is not forced into contact with the afflicted region A.

The disclosed embodiment is representative of the preferred form of the invention, but is intended to be illustrative rather than definitive thereof. The invention is defined in the claims.

I claim:

1. A foot cushion device for relieving pressure and discomfort on an afflicted region of the sole of a person's foot, said device comprising:

a foam pad having an elastic memory enabling said pad to deform under the weight of a person and recover its shape after each of repeated deformations, said pad being of substantially uniform thickness and having a lateral width approximating the width of such person's foot, an upper foot-engaging surface adapted to occupy a position against the sole of such person's foot in the vicinity of the afflicted region, a lower surface spaced from said upper surface by the thickness of said pad, said pad having a notch extending laterally inwardly into said pad from one side thereof and spanning said upper and lower surfaces, thereby providing a recess for the accommodation of the afflicted region;

a non-adhesive band of elastic material having opposite ends and of sufficient length and elasticity as to enable said band to encircle both such person's foot and said pad so as to hold said pad in said position against such person's foot; and attaching means for securing said ends of said band to one another.

2. The device of claim 1 wherein said attaching means comprises a first swatch of hooked fabric material fixed to said lower surface of said pad and releasably engaged with one of said ends of said band for releasably securing said one end to said pad.

3. The device of claim 2 wherein the lower surface of said pad has a pair of spaced apart sections adjacent said notch that are free of said hooked fabric material so as to be movable relative to said band.

4. The device of claim 2 wherein said first swatch is adhered to said pad.

5. The device of claim 2 wherein said attaching means includes a second swatch of said hooked fabric material fixed to the other of said ends of said band, said other end overlapping said one end of said band.

6. The device of claim 2 wherein said pad is formed of open-cell polyurethane foam.

7. The device of claim 6 wherein said foam has a density of about 1.8 to 2.0 g/cm$^3$.

8. The device of claim 7 wherein the thickness of said pad is about 2 inches.

9. The device of claim 7 wherein said pad has a width of about 3 inches and a length of about 4 inches.

10. The device of claim 2 wherein said band is fabricated of non-adhesive material.

11. The device of claim 10 wherein said band has a width of about 4 inches and a length of about 12 inches.

12. The device of claim 2 wherein said notch has spaced parallel side walls joined at corresponding ends by an interconnecting wall having a semicircular configuration to provide said notch with a U-shaped configuration when viewed from said upper surface of said pad.

13. The device of claim 12 wherein said notch has a width of about 1 inch and extends into said pad a distance of about 1 inch.

14. A foot cushion device for use by a person having a Charcot joint affliction protruding from the lower instep region of the foot to relieve pressure and discomfort normally associated with the wearing of foot apparel by a person having such an affliction, said device comprising:

a substantially uniform thickness pan of open cell polyurethane foam having a density of between 1.8 and 2.0 g/cm$^3$ and height, width, and length dimensions of 2 inches, 3 inches, and 4 inches, respectively, said pad being capable of occupying a position against and under the sole of a person's foot and having an elastic memory enabling said pad to deform under the weight of the person and recover its original shape after each of repeated deformations, said pad having a relatively flat upper foot-engaging surface adapted to bear against the sole of the person's foot in the vicinity of the affected Charcot joint region, a relatively flat lower surface spaced from and parallel to said upper surface, and a notch extending laterally inwardly into said pad from one side thereof to a depth of about 1 inch and having a width of about 1 inch and being open to said upper and lower surfaces to provide an unobstructed recess for accommodation of the afflicted Charcot joint region, said density and height of said pad being such that when said pad is compressed against the foot of such person by the weight of such person the compressed height of said pad adjacent said notch remains sufficiently great to accommodate the afflicted Charcot joint region wholly within said notch;

a first swatch of hooked anchoring fabric secured to said lower surface of said foam pad; and an elastic band fabricated of non-chafing, non-adhesive material having opposite ends and a length of about 12 inches between said ends to enable said band to encircle such user's foot and said pad so as to hold said pad in said position against such user's foot, said band material being compatible with said hooked anchoring fabric to enable a first one of said ends of said band removably to be attached to said first swatch to secure said one end to said block, the other of said ends of said band mounting a second swatch of said hooked anchoring fabric to enable said other end to be overlapped onto said one end to secure said second swatch releasably to said band material at a location underlying said lower surface of said pad.

* * * * *